United States Patent [19]

Brabandt et al.

[11] Patent Number: 4,702,115

[45] Date of Patent: Oct. 27, 1987

[54] SAMPLE INJECTION TIMER FOR CHROMATOGRAPHIC APPARATUS

[76] Inventors: Earl Brabandt, 6424 Sunnyvfield Way, Sacramento, Calif. 95823; Robert R. Freeman, 9160 Madison Ave., Fair Oaks, Calif. 95662

[21] Appl. No.: 833,306

[22] Filed: Feb. 25, 1986

[51] Int. Cl.$^4$ ............................................. G01N 30/12
[52] U.S. Cl. ................................. 73/864.85; 73/863.01
[58] Field of Search ........... 73/864.85, 864.81, 864.87, 73/23.1, 864.82, 864.83, 864.84, 864.86, 863.01

[56] References Cited

U.S. PATENT DOCUMENTS

| | | | |
|---|---|---|---|
| 3,630,088 | 12/1971 | Sawyer et al. | 73/864.81 X |
| 3,649,204 | 3/1972 | Farr | 73/864.85 X |
| 3,668,834 | 6/1972 | Deans | 73/864.81 X |
| 3,800,593 | 4/1974 | Bradley | 73/864.81 |
| 3,940,994 | 3/1976 | Klee et al. | 73/864.81 |
| 4,035,168 | 7/1977 | Jennings | 73/864.85 |
| 4,347,215 | 8/1982 | Sisti et al. | 73/864.87 X |
| 4,414,857 | 11/1983 | Brazhnikov et al. | 73/864.87 X |

FOREIGN PATENT DOCUMENTS

| | | | |
|---|---|---|---|
| 24580 | 2/1977 | Japan | 73/864.81 |
| 578584 | 10/1977 | U.S.S.R. | 73/864.81 |

OTHER PUBLICATIONS

"Automatic Vapor Sampling for Gas Chromatographic Analysis"; *Analytical Chemistry*, vol. 38, No. 8, Jul. 1966, pp. 1097-1098; G. Szekely et al.

*Primary Examiner*—Stewart J. Levy
*Assistant Examiner*—Tom Noland

[57] ABSTRACT

A method and apparatus for detecting the injection of a solvent borne sample into the injector port of a chromatograph having a carrier gas flow path for pressurizing the port. The gas pressure in a region adjacent the injector port is monitored. When vaporization of the solvent causes the carrier gas pressure to rise above the steady state value by a threshold amount, a control signal is generated which serves as an accurate time reference for the moment of sample injection into the injector port. The carrier gas pressure is monitored by time averaging the instantaneous carrier gas pressure and differentially sensing the instantaneous carrier gas pressure and the time averaged instantaneous carrier gas pressure. The time averaging is preferably done by flow restricting the carrier gas and accumulating the flow restricted carrier gas in a chamber.

20 Claims, 4 Drawing Figures

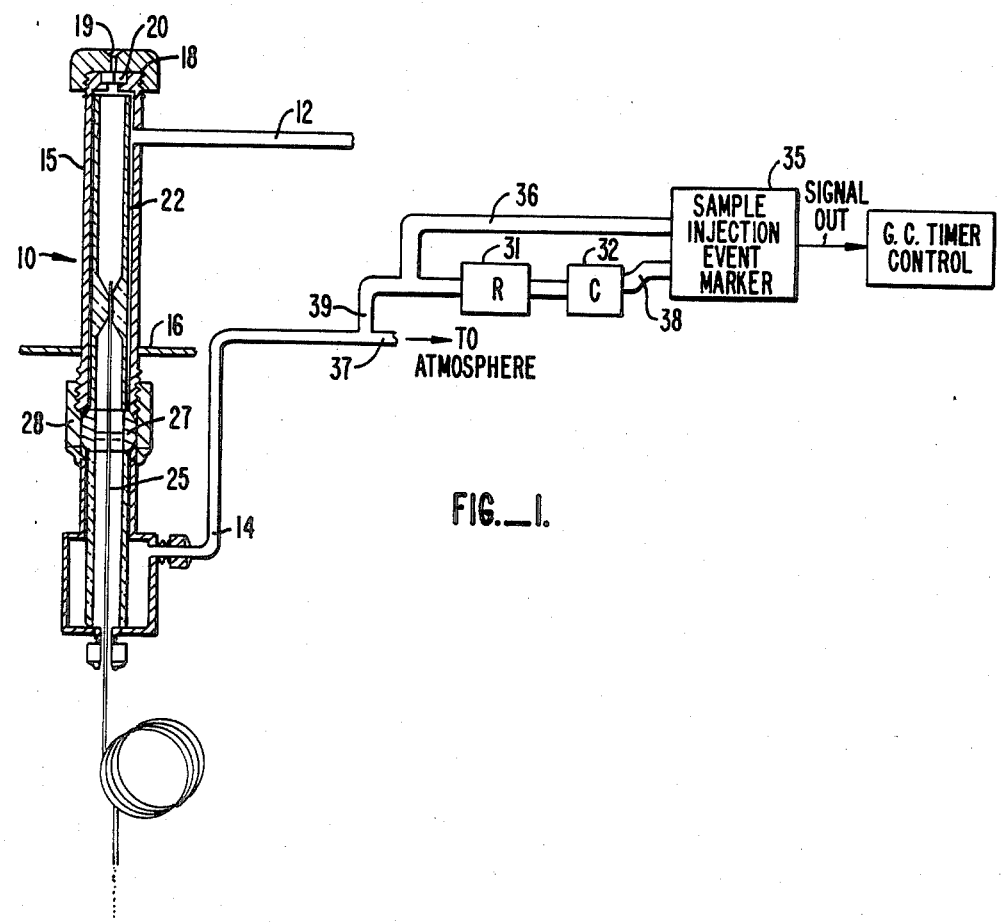
FIG._1.
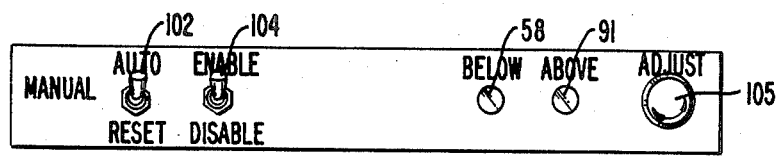
FIG._3.
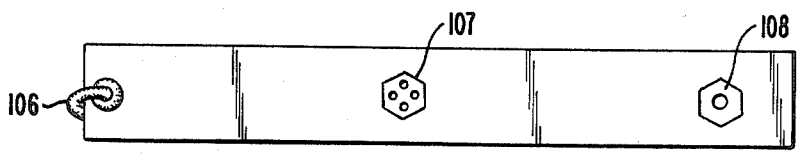
FIG._4.

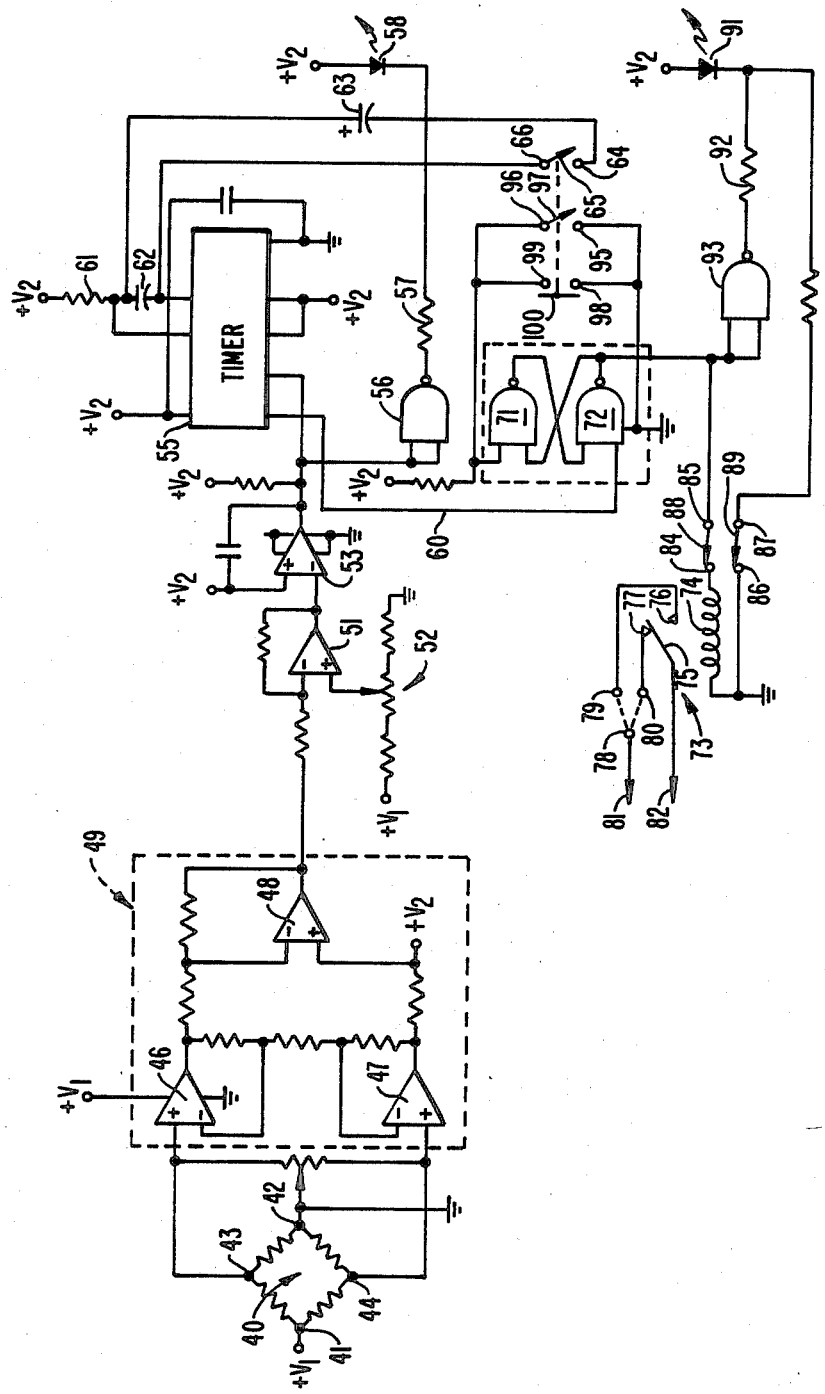
FIG._2.

4,702,115

SAMPLE INJECTION TIMER FOR CHROMATOGRAPHIC APPARATUS

BACKGROUND OF THE INVENTION

This invention relates to chromatographic apparatus used to identify the chemical constituents of material samples. More particularly, this invention relates to control circuitry used in connection with such chromatographic devices.

Chromatographic devices are known which are used in the analysis of chemical constituents in sample materials. Such devices typically include an injector port for enabling the injection of a sample to be analyzed into the inlet portion of the chromatographic device, a column providing a transport path for the injected sample, a detector positioned at the end of the column for generating variable amplitude samples representative of the quantity of analyte (sample material) passing through the detector, and electromechanical circuitry for recording the detector signal and for controlling the operation of the various electrical and mechanical components of the device. In gas chromatographs, a carrier gas inlet is provided at the injector port for enabling the introduction of a carrier gas, which serves as the transport vehicle through the column for samples introduced into the injector port. In capillary column chromatographs, an outlet, usually termed a purge or split exit line, is typically included to provide an outlet path to the atmosphere or ambient for the carrier gas and also maintain the fluid pressure between the inlet and the outlet at some predetermined value or within some predetermined range.

One of the major information components generated during chromatographic analysis of a sample is the length of time between the start of the sample injection to the appearance of a particular chromatographic peak in the detector signal: by measuring the precise time interval, the retention time of a given chromatographic peak in the detector signal can be compared with known retention times of individual chemical constituents in order to identify the particular constituent associated to a given chromatographic peak in the detector signal. Consequently, a necessary step in the chromatographic analysis process is the generation of a starting reference time signal. In the past, the starting time reference signal has been provided in one of two ways: manually or automatically. According to a first manual technique, a manual switch is provided for a timer or clock associated with the chromatographic apparatus and the operator manually actuates the switch at the same time the sample is manually injected into the injector port. In a second manual technique, a mechanical switch is provided at the injector port in such a location that the switch is mechanically triggered upon insertion of a syringe needle into the injector port.

Both of the above manual techniques for providing an initial timing signal suffer from the disadvantage of providing a relatively imprecise definition of the instant of sample injection. In the first manual technique, the accuracy of the manual switch closure depends upon the ability of the operator to inject the sample and operate the switch simultaneously. The second manual technique employing the mechanical switch measures the instant of insertion of the syringe needle into the injector port, which may or may not coincide with the instant at which the sample is released from the syringe. Perhaps most importantly, however, neither technique provides a precise indication of the moment at which the sample enters the injector port. As a consequence of the above disadvantages, an element of uncertainty is introduced into the chromatographic analysis process, which is highly undesirable.

The automatic technique for generating the starting time reference signal employs a complicated and expensive pneumatic or electromechanical apparatus, usually sold as auxiliary equipment, which generates a signal when a sample containing syringe is actuated to mechanically inject a sample into the injector port. Since this apparatus is used for automatic loading of samples into the syringe and automatic sample injection into the injection port, it is not adapted to be conveniently employed to generate a starting time reference signal for single runs or for runs of only a few samples. In addition, since the actuation of the syringe is the event being monitored, the starting time reference signal generated by this technique is not an exact measure of the time at which the sample actually enters the injector port.

SUMMARY OF THE INVENTION

The invention comprises a method and apparatus for providing a precise initial timing reference signal specifying the instant of sample injection into the injector port of a chromatographic apparatus, which is highly reliable in operation, relatively inexpensive to implement and devoid of the disadvantages noted above.

From a method standpoint, the invention includes the steps of detecting the injection of a solvent borne sample into the injector port of the chromatograph having a carrier gas flow path for pressurizing the port, the method comprising the steps of monitoring the carrier gas pressure in a region adjacent the injector port, and generating a control signal when vaporization of the solvent causes the carrier gas pressure to rise above the steady state value by a threshold amount. The step of monitoring preferably includes the steps of providing a moving time average of the carrier gas pressure and differentially sensing the carrier gas pressure and the time average carrier gas pressure. The step of integrating includes the steps of flow restricting the carrier gas, and accumulating the flow restricted carrier gas in a chamber; while the step of generating includes the step of establishing the threshold amount. The method can be used to time the moment of injection of a solvent borne sample into the injector port by including the step of injecting a solvent borne sample into the injector port while performing the step of monitoring.

From an apparatus standpoint, the invention comprises a system for signalling the injection of a sample in a chromatograph having an injector port for receiving a fluid sample, and a fluid line coupled to an injector port containing a carrier fluid under pressure, the system comprising transducer means for generating a signal representative of the fluid pressure in the injector port; means coupled to the transducer means for time averaging the fluid pressure; and event marker means coupled to the transducer means and responsive to a signal representative of a differential pressure of a selected threshold magnitude caused by injection of a sample into the chromatograph injector port for generating a control signal specifying the beginning of a sample run in the chromatograph. The fluid pressure time averaging means preferably comprises a flow restrictor and a flow chamber coupled in series which provide a time constant preferably lying in the range from about 3 to about 6 seconds.

The event marker means includes adjustable means for establishing an electrical threshold signal representative of the differential pressure threshold magnitude, and the system preferably includes visible indicator means for indicating the proper setting of the electrical threshold signal.

The event marker means preferably includes an amplifier circuit coupled to the transducer means for amplifying the transducer signal, means for establishing an electrical threshold signal representative of the differential pressure threshold magnitude, comparator means coupled to the amplifier circuit and the electrical threshold signal establishing means for generating a trigger signal when the amplified transducer signal exceeds the electrical threshold signal by a selected amount, and means responsive to the trigger signal for providing the control signal.

The means for providing the control signal preferably includes logic means having an output for manifesting the control signal and an input, and pulse generator means having an input coupled to the trigger signal generating means and an output coupled to the input of the logic means for generating a logic means operating pulse. The system preferably includes visible indicator means coupled to the pulse generator means for indicating the generation of the logic means operating pulse.

The pulse generator means preferably includes first switch means for enabling selection of a logic means operating pulse having one or two possible periods, and the system preferably further includes second switching means coupled to the pulse generating means for enabling alternate selection of a manual operating mode and an automatic operating mode for the pulse generator means, and third switching means coupled to the pulse generator means for manually resetting the pulse generator means, the first, second and third switch means preferably being mechanically interconnected. An additional switch means is also included for disabling the relay means during initial adjustment of the system prior to the injection of a sample.

The invention enables the detection of a carrier fluid pulse which is generated at the precise moment that the sample enters the injection port of the chromatograph. In gas chromatograph applications, the fluid is a carrier gas which pressurizes the injector port into which a solvent borne sample is injected, typically by means of a needle tipped syringe. The detected pulse can be used to automatically commence the operation of the associated chromatographic device, including the operation of a strip chart recorder typically incorporated into such devices. By eliminating human error and detecting the instanteous moment of sample injection, a highly accurate time starting reference is provided by the invention.

For a fuller understanding of the nature and advantages of the invention, reference should be had to the ensuing detailed description taken in conjunction with the accompanying drawings.

BRIEF DESCRIPTION OF THE DRAWINGS

FIG. 1 is a schematic diagram of a preferred embodiment of the invention and the associated gas chromatograph;

FIG. 2 is an electrical circuit diagram illustrating the circuitry incorporated into the preferred embodiment of the invention;

FIG. 3 is a view of the front panel of the preferred embodiment; and

FIG. 4 is a view of the rear panel of the preferred embodiment of the invention.

DESCRIPTION OF THE PREFERRED EMBODIMENT

Turning now to the drawings, FIG. 1 illustrates in block diagram form the preferred embodiment of the invention and pertinent portions of an associated gas chromatograph device. As seen in this Figure, the gas chromatograph device includes an injector port generally designated with reference numeral 10 having a carrier gas inlet 12 and a carrier gas outlet 14, typically designated a split exit line or a purge exit line. The injector port includes a tubular member 15 which passes through an aperture in the upper wall 16 of the gas chromatograph oven (not shown). Threadably attached to the upper end of tubular member 15 is a cap nut 18 providing a needle inlet guide 19 for the needle tip of a conventional syringe and a septum 20 for enabling the needle to be inserted into the interior of a glass liner 22.

The upper end of a capillary column 25, which is preferably a type 1235032 column available from J&W Scientific Co. of Rancho Cordova, Calif., is arranged in the lower chamber of liner 22 and held in place by means of a conventional ferrule assembly 27 captured by means of a sleeve nut 28 threadably engaged with the lower end of tubular member 15. The capillary column extends down into the oven region of the associated chromatographic device and provides a transport path of precisely controlled inner diameter for a solvent borne sample injected into the glass liner 22 in a conventional fashion.

Attached to the purge exit line 14 is a flow restrictor 31 having an outlet coupled to the inlet of an accumulation chamber 32. The flow restrictor 31 preferably comprises a tubular member having an inner diameter which is relatively small in comparison to the inner diameter of the purge exit line 14. For example, for a purge exit line having an inner diameter of 0.035 inch, the inner diameter of restrictor 31 may lie in the range from about 0.003 inch to about 0.004 inch. The accumulation chamber C is a fluid cavity having a volumetric capacity, in the preferred embodiment, of about 5 ml. The purpose of the combination of the serially connected flow restrictor 31 and accumulation chamber 32 is to perform a time averaging of the instanteous fluid pressure in the purge exit line 14, and to present this time averaged physical quantity to a first input of a differential pressure transducer forming part of the sample injection event marker 35. The other fluid inlet to the differential pressure transducer incorporated into sample injection event marker 35 is coupled directly to the purge exit line 14 by means of conventional fluid conduit 36. The purge exit line 14 also has a branch 37 coupled to ambient to provide an exhaust path for carrier gas flowing from inlet conduit 12, through the body of tubular member 15 and through purge exit line 14. As with conventional gas chromatographs having a carrier gas flow path, the purpose of the carrier gas flow path described above is to pressurize the internal volume of the injector port so that a sample injected into glass liner 22 is forced into the capillary column 25.

As noted above, sample injection event marker 35 has two fluid inlets: viz., direct inlet 36 which communicates the instanteous carrier gas pressure to one side of a differential pressure transducer, and second inlet 38 which couples time averaged value of the instantenous carrier gas pressure to the second side of the differential pressure transducer incorporated into sample injection event marker 35. Whenever the instantaneous value of the carrier gas pressure rises above the time averaged carrier gas pressure value by a threshold amount, the sample injection event marker 35 generates an electrical output signal which is coupled as a control signal to any appropriate user auxiliary device, such as a gas chromatograph timer control input, a gas chromatograph event board, a chart recorder or an integrating chart recorder. This signal is thus used to control the start of a chromatographic run, for example, by initiating the operation of a chart recorder or any other measuring device incorporated into the associated gas chromatographic system. The increase in the carrier gas pressure is caused by vaporization of the solvent within the injector port upon heating when the solvent borne sample enters the heated region below the upper wall 16 of the gas chromatograph.

FIG. 2 illustrates the electronic circuitry incorporated into the sample injection event marker 35. As seen in this Figure, a differential pressure transducer 40 has a first power terminal 41 coupled to a suitable supply voltage $V_1$, preferably 12 volts DC; and a second power terminal 42 coupled to ground reference. The differential pressure transducer preferably comprises a type 125 PC05D1 pressure sensor available from the micro-switch division of Honeywell Corporation. The two output terminals 43, 44 of the differential pressure transducer 40 are coupled to the positive inputs of a pair of operational amplifiers 46, 47. The negative input terminals of amplifiers 46, 47 are coupled to the illustrated terminals of a resistance ladder network. The outputs of the two amplifiers 46, 47 are each coupled via a suitable input resistance to the opposite input terminals of an amplifier 48. The circuit 49 comprising amplifiers 46–48 and the resistances shown comprises a differential amplifier system, which generates an output signal representative of the output signal generated by the differential pressure transducer in response to pressure differences between the instantaneous carrier gas pressure present in conduit 36 (FIG. 1) and the integrated carrier gas pressure value present in conduit 38.

The output of the differential amplifier circuit 49 is coupled via a suitable input resistance to the negative input of an operational amplifier 51. The positive input of amplifier 51 is coupled to reference voltage source $V_1$ by means of an adjustable potentiometer 52. The purpose of adjustable potentiometer 52 is to provide a variable electrical offset voltage which is summed with the output signal from the differential amplifier circuit 49 by operational amplifier 51. This variable offset voltage is required since the range on absolute value of the amplifier circuit 49 output signal is relatively wide, due to variation in the carrier gas pressure, the time content of the restrictor 31 chamber 32, the viscosity of the carrier gas, the operating temperature, and various parameters of the electronic components. Also, the offset voltage enables the operator to adjust the circuitry (in the manner described below) to substantially eliminate false triggering due to noise in the signal output from amplifier circuit 49.

The output of amplifier 51 is coupled to the negative input of an amplifier 53 configured as a voltage comparator and having a positive input terminal coupled to a suitable reference voltage source $V_2$, preferably 5 volts DC.

Amplifiers 46–48, 51 and 53 are preferably type LM324 operational amplifiers.

The output of amplifier 53 provides the trigger signal, which is generated whenever the difference between the instantenous carrier gas pressure and the time averaged carrier gas pressure exceeds a threshold amount established by potentiometer 52. The trigger signal output from amplifier 53 is coupled to the trigger input of a one shot timer circuit 55. In addition, the output signal from amplifier 53 is coupled to the inputs of a NAND gate 56 coupled via a suitable resistance 57 to the cathode of a first light emitting diode 58. The anode of diode 58 is coupled to voltage reference source $V_2$. Whenever the level of the signal output from amplifier 53 lies below the fixed threshold value of source $V_2$, light emitting diode 58 is illuminated to signify that the system is ready for operation and has a properly adjusted variable threshold setting.

Timer 55, which preferably comprises a type 74121 integrated circuit, produces a pulse output signal on conductor 60, the pulse having an output value depending upon the R-C time constant provided to timer 55 at any given moment. The R-C time constant is partially determined by a resistance 61 and a capacitor 62 connected as shown. The time constant can be changed to a second value in the FIG. 2 circuit by the addition of a second capacitor 63 connected to a first switch terminal 64 and the junction between resistance 61 and capacitor 62. Whenever blade 65 closes the connection between terminal 64 and terminal 66, the time constant of the timer 55 is longer than the time constant afforded by resistance 61 and capacitance 62. Consequently, the width of the negative going pulse generated by timer 55 is dependent upon whether additional capacitor 63 is inserted into the timer circuit by closing the switch comprising elements 64–66.

A pair of cross coupled NAND gates 71, 72 are used to control the operation of a relay 73, the relay 73 having a relay coil 74, a moveable blade 75, alternate contacts 76, 77 and fixed terminals 78–80. Alternate contacts 76, 77 and alternate fixed terminal 79, 80 are provided in order to permit the unit to be compatible with a gas chromatograph timer control or event board having either a normally opened or normally closed input switching requirement. For example, for a timer control requiring a normally open switch input, an electrically conductive jumper is connected between terminals 78 and 79 to render contact 76 the active contact. For a timer control requiring a normally closed input, a jumper is provided between terminals 78 and 80 to render normally closed contact 77 the active contact. Whenever coil 74 is energized in the manner described below, the moveable blade 75 is switched between contacts 76 and 77 to change the state of the electrical path between output terminals 81, 82. A double pole single throw switch comprising terminals 84–87 and blades 88, 89 is provided to disable the output of the FIG. 2 circuit during adjustment of the threshold potentiometer 52.

As noted above, cross coupled NAND gates 71, 72 control the state of relay 73. In addition, these gates also control the state of a second light emitting diode 91 having an anode coupled to reference voltage source $V_2$ and cathode coupled via a suitable resistance 92 to the output of a NAND gate 93. The inputs of NAND gate 93 are coupled to the output of NAND gate 72 as shown.

A switch comprising fixed terminals 95, 96 and a moveable blade 97 is coupled between reference ground and the upper input of NAND gate 71. A second momentary contact switch comprising fixed terminals 98, 99 and a spring loaded contact blade 100 is coupled in parallel with the switch composed of elements 95–97. Blade 65, 97 and 100 are mechanically interlinked as suggested by the broken line. The position of blades 65, 97 and 100 determines the mode of operation of the circuit of FIG. 2: viz., automatic, manual or reset.

In the automatic mode of operation blades 65 and 97 are in the closed position and blade 100 is in the open position. In these positions, capacitor 63 is inserted into the timer circuit and the upper input terminal of NAND gate 71 is permanently grounded. In the manual mode of operation, the blades 65, 97 and 100 are all open as illustrated. In the reset mode of operation, blade 65 and 97 are open and blade 100 is momentarily moved to the closed state and returns to the open state when manually released.

In operation, with power applied to the circuitry shown in FIG. 2 and the disable switch (elements 84–89) in the open position to disable the relay 73, the threshold is adjusted in the following manner. When the purge exit line 14 is pressurized to the desired value (determined by the chromatograph operator), potentiometer 52 is adjusted to a position at which the LED 58 becomes illuminated. Specifically, if LED 58 is extinguished, potentiometer 52 is adjusted to the position at which LED 58 becomes illuminated. If LED 58 is initially illuminated, potentiometer 52 is adjusted in the proper direction until LED 58 is extinguished, and then in the opposite direction until LED 58 is illuminated. LED 58 remains illuminated whenever the threshold setting established by potentiometer 52 is just below the trigger point of the circuit.

With the threshold properly adjusted as indicated by the illumination of LED 58, and with the disable switch (elements 84–89) still open, blade 100 is moved to the reset position which temporarily grounds the upper input to NAND gate 71. The lower input to NAND gate 72 is normally at a high level in the absence of a trigger pulse output from timer 55; since the upper input to NAND gate 71 is reduced to ground level by operating the reset switch, the other input to NAND gate 72 is momentarily raised to the high level and the output of NAND gate 72, which is momentarily enabled, drops to the low logic level. When the reset switch is released, the upper input of NAND gate 71 is raised to the high logic state: however, since the lower input to NAND gate 71 is still low, the output of NAND gate 71 remains high and the output of NAND gate 72 remains low. In this condition, and with the blades 65, 97 and 100 all in the open state illustrated, the system is in the manual mode of operation. The disable switch is now closed.

Whenever a pressure pulse in purge exit line 14 is sensed by transducer 40 and exceeds the system threshold value, a trigger pulse is generated by amplifier 53. This pulse, which is a negative going pulse, momentarily extinguishes LED 58 and triggers timer 55. Timer 55, in turn, generates a negative going pulse which is conducted via conductor 60 to the lower input of NAND gate 72. This causes the output of NAND gate 72 to rise to the high logic level which enables NAND gate 93, thereby illuminating LED 91 and energizing relay 73. When the output of NAND gate 72 rises to the high logic level, the output of NAND gate 71 falls to the low logic level, thereby disabling NAND gate 72.

Thus, when the negative going pulse generated by timer 55 terminates, gates 71, 72 remain in such a logic state that the relay 73 and LED 91 remain energized until NAND gates 71, 72 are reset. To reset gates 71, 72 in the manual mode of operation, blade 100 is momentarily closed, which causes NAND gate 71 to generate a high logic level output, and this in turn causes NAND gate 72 to generate a low logic level output signal, thereby disabling relay 73 and extinguishing LED 91.

To switch the circuit of FIG. 2 to the automatic mode of operation, blades 65 and 97 are closed. This causes the upper input of NAND gate 71 to permanently grounded and inserts capacitor 63 into the timing network for timer 55. At the start of the automatic mode of operation, the output of NAND gate 71 is at the high logic level and the output of NAND gate 72 is at the low logic level. When a trigger pulse is generated by amplifier 53, timer 55 generates a corresponding pulse having a different (longer) period, due to the added capacitance of capacitor 63. When the negative going edge of the timer 55 output pulse is coupled to the lower input of NAND gate 72, the output of NAND gate 72 rises to the high logic level and remains there for the duration of the output pulse from timer 55. This energizes relay 73 and illuminates LED 91. After the negative going pulse presented to the lower input of NAND gate 72 terminates and rises to the high level, the output of NAND gate 72 falls to the low logic level, thereby deactuating relay 73 and extinguishing LED 91.

FIG. 3 illustrates the front panel of the housing for the circuitry of FIG. 2. As seen in this Figure, the three blade switch has a toggle lever 102 which enables the switch to be placed in the auto, manual and reset positions. To the right of handle 102 is a handle 104 for controlling the state of the disable switch. The two LED's 58, 91 are mounted to the right of the switch handles 102, 104, and an adjustment knob 105, which is coupled to an input shaft for controlling potentiometer 52, is mounted to the right of LED 91.

FIG. 4 shows the rear panel of the housing for the circuitry of FIG. 2. As seen in this Figure, a power cord 106 is provided for supplying the reference voltages $V_1$, $V_2$. In the middle of the panel is an output socket 107 which contains output terminals 81, 82 of the relay 73. To the far right of the panel, a bulkhead fitting 108 is provided which is coupled to branch 39 of the purge exit line 14 (FIG. 1). The flow restrictor 31 and accumulating chamber 32 are mounted within the housing.

The invention affords a highly reliable method and system for detecting the exact instant at which a solvent borne sample is injected into the inlet system of a gas chromatograph. The use of the differential pressure transducer accommodates the dynamic and operating range requirements imposed by chromatographic systems. Specifically, as noted above, the operating pressure in the carrier gas flow path can vary from about 2 psig to about 200 psig; while the magnitude of the pressure pulse varies from about 0.05 psig to about 0.5 psig. In spite of these severe requirements, the invention has been found to operate in a highly reliable manner. By automatically generating a control signal at the instant of solvent vaporization, the event starting time is precisely indicated to the associated user device, thus assuring repeatability of results and accuracy of the initial starting reference point. By providing both manual and automatic modes of operation, the invention affords flexibility of operation and accommodates both single sample runs and plural successive sample runs. It should be noted that the time constant selected for the automatic mode of operation in the preferred embodiment is about 15 seconds, while the time constant afforded by the manual mode of operation is about 0.1 second. It should be further noted that time constant provided by the fluid integrator comprising flow restrictor 31 and accumulating chamber 32 is about 6 seconds, and with this time constant the fluid portion of the timer achieves 90% stabilization within approximately 5 time constants or 30 seconds. Thus, the warm up time of the system is relatively short and does not interfere with the normal mode of operation of the associated chromatographic equipment.

While the above provides a full and complete disclosure of the preferred embodiment of the invention, various modifications, alternate equivalents and constructions may be employed without departing from the true spirit and scope of the invention. For example, while the invention has been described with reference to a capillary column gas chromatograph, it is equally applicable to a packed column chromatograph. Further, while the pressure sensing components have been illustrated as coupled to the split/purge line 14, they may also be coupled to the inlet line 12. If desired, a separate opening may be formed in the injector port member 15 to couple the fluid pressure to the pressure sensing components. Further, while the time averaging of the carrier gas pressure has been illustrated using physical analog elements—viz., restrictor 31 and chamber 32—these functions can be performed by equivalent electronic analog or digital circuits, if desired. Moreover, different transducers, amplifiers, integrated circuits and other functionally equivalent circuits (such as switching transistors, gates and the like for relay 73) may be employed; and other time constants may be selected, as desired. Therefore, the above descriptions and illustrations should not be construed as limiting the scope of the invention which is defined by the appended claims.

What is claimed is:

1. A system for signalling the injection of a sample in a chromatograph having an injector port for receiving a fluid sample and a carrier fluid path, said system comprising:
    differential pressure transducer means having first and second fluid inlets for generating a signal representative of the differential pressure between said first and second fluid inlets, a first one of said first and second fluid inlets being adapted to be coupled to the carrier fluid path;
    means having an inlet adapted to be coupled to the carrier fluid path and an outlet coupled to the other one of said first and second fluid inlets for time averaging the fluid pressure in the carrier fluid path; and
    event marker means coupled to said transducer means and responsive to a signal representative of a differential pressure of a selected threshold magnitude caused by injection of a sample into the chromatograph injector port for generating a control signal specifying the beginning of a sample run in the associated chromatograph in response to the injection of a sample in the injector port.

2. The invention of claim 1 wherein said time averaging means comprises a flow restrictor and a flow chamber coupled in series.

3. The invention of claim 1 wherein said event marker means includes adjustable means for establishing an electrical threshold signal representative of said differential pressure threshold magnitude.

4. The invention of claim 3 further including visible indicator means for indicating the proper setting of said electrical threshold signal.

5. The invention of claim 1 wherein said event marker means includes an amplifier circuit means coupled to said transducer means for amplifying said transducer signal, means for establishing an electrical threshold signal representative of said differential pressure threshold magnitude, comparator means coupled to said amplifier circuit means and said electrical threshold signal establishing means for generating a trigger signal when the amplified transducer signal exceeds said electrical threshold signal by a selected amount, and means responsive to said trigger signal for providing said control signal.

6. The invention of claim 5 wherein said means for providing said control signal includes logic means having an output for manifesting said control signal and an input, and pulse generator means having an input coupled to said trigger signal generating means and an output coupled to said input of said logic means for generating a relay means operating pulse.

7. The invention of claim 6 wherein said logic means comprises a relay.

8. The invention of claim 6 further including visible indicator means coupled to said pulse generator means for indicating the generation of said logic means operating pulse.

9. The invention of claim 6 wherein said pulse generator means includes first switch means for enabling selection of a logic means operating pulse having one of two possible periods.

10. The invention of claim 6 further including second switch means coupled to said pulse generator means for enabling alternate selection of a manual operating mode and an automatic operating mode for said pulse generator means.

11. The invention of claim 6 further including third switch means coupled to said pulse generator means for manually resetting said pulse generator means.

12. The invention of claim 6 further including first switch means coupled to said pulse generator means for enabling selection of a logic means operating pulse having one of two possible periods, second switch means coupled to said pulse generator means for enabling alternate selection of a manual operating mode and an automatic operating mode for said pulse generator means, and third switch means coupled to said pulse generator means for manually resetting said pulse generator means, said first, second and third switch means being mechanically interconnected.

13. The invention of claim 6 further including fourth switch means for disabling said logic means.

14. A method for detecting the injection of a solvent borne sample into the injector port of a chromatograph having a carrier gas flow path for pressurizing the port, said method comprising the steps of:
    (a) monitoring the carrier gas pressure in a region adjacent the injector port; and
    (b) generating a control signal when vaporization of the solvent causes the carrier gas pressure to rise above the steady state value by a threshold amount.

15. The invention of claim 14 wherein said step (b) of generating includes the step of establishing said threshold amount.

16. A method for the timing the moment of injection of a solvent borne sample into the injector port of a chromatograph having a carrier gas flow path for pressurizing the port, said method comprising the steps of:
(a) monitoring the carrier gas pressure in the region adjacent the injector port;
(b) injecting a solvent borne sample into the injector port; and
(c) generating a control signal when vaporization of the solvent causes the carrier gas pressure to rise above the steady state value by a threshold amount.

17. A method for detecting the injection of a solvent borne sample into the injector port of a chromatograph having a carrier gas flow path for pressurizing the port, said method comprising the steps of:
(a) monitoring the carrier gas pressure in a region adjacent the injector port by (i) time averaging the instantaneous carrier gas pressure and (iii) differentially sensing the instantaneous carrier gas pressure and the time averaged instantaneous carrier gas pressure; and
(b) generating a control signal when vaporization of the solvent causes the carrier gas pressure to rise above the steady state value by a threshold amount.

18. The invention of claim 17 wherein said step (i) of time averaging comprises the steps of flow restricting the carrier gas and accumulating the flow restricted carrier gas in a chamber.

19. The invention of claim 17 wherein said step (b) of generating includes the step of establishing said threshold amount.

20. A method for timing the moment of injection of a solvent borne sample into the injector port of a chromatograph having a carrier gas flow path for pressurizing the port, said method comprising the steps of:
(a) monitoring the carrier gas pressure in the region adjacent the injector port by (i) time averaging the instantaneous carrier gas pressure and (ii) differentially sensing instantaneous carrier gas pressure and the time averaged instantaneous carrier gas pressure;
(b) injecting a solvent borne sample into the injector port; and
(c) generating a control signal when vaporization of the solvent causes the carrier gas pressure to rise above the steady state value by a threshold amount.

* * * * *